US010856899B2

(12) United States Patent
Connell (10) Patent No.: US 10,856,899 B2
(45) Date of Patent: Dec. 8, 2020

(54) DEVICE AND A METHOD FOR GUIDING A BORING TOOL, A GUIDE WIRE OR AN INSTRUMENT INTO ENGAGEMENT WITH AN OCCLUSION IN A VESSEL OR A WALL OF THE VESSEL IN THE BODY OF A HUMAN OR ANIMAL SUBJECT (71) Applicant: CAPSOS MEDICAL LIMITED, Galway (IE)

(72) Inventor: Ian Michael Connell, County Galway (IE)

(73) Assignee: CAPSOS MEDICAL LIMITED, Galway (IE)

(*) Notice: Subject to any disclaimer, the term of this patent is extended or adjusted under 35 U.S.C. 154(b) by 161 days.

(21) Appl. No.: 16/078,520

(22) PCT Filed: Feb. 22, 2017

(86) PCT No.: PCT/IE2017/000003
§ 371 (c)(1),
(2) Date: Aug. 21, 2018

(87) PCT Pub. No.: WO2017/145139
PCT Pub. Date: Aug. 31, 2017

(65) Prior Publication Data
US 2019/0046229 A1 Feb. 14, 2019

(30) Foreign Application Priority Data

Feb. 22, 2016 (IE) .................................. S2016/0059

(51) Int. Cl.
A61B 17/3207 (2006.01)
A61B 17/3205 (2006.01)
(Continued)

(52) U.S. Cl.
CPC .. *A61B 17/320758* (2013.01); *A61B 17/3207* (2013.01); *A61B 17/32053* (2013.01);
(Continued)

(58) Field of Classification Search
CPC ...... A61B 17/320758; A61B 17/32002; A61B 17/32053; A61B 2017/320032;
(Continued)

(56) References Cited

U.S. PATENT DOCUMENTS 5,078,723 A * 1/1992 Dance ................. A61B 17/3207
604/22
5,409,470 A * 4/1995 McIntyre ............... A61M 25/09
604/528

(Continued)

FOREIGN PATENT DOCUMENTS

WO 2011/129915 A2 10/2011
WO 2012/123930 A2 9/2012

OTHER PUBLICATIONS

International Search Report for PCT/IE 2017/000003 dated May 4, 2017 [PCT/ISA/210].

(Continued)

Primary Examiner — Tan-Uyen T Ho
Assistant Examiner — Charles M Wei
(74) Attorney, Agent, or Firm — Sughrue Mion, PLLC (57) ABSTRACT A balloon catheter (1) including a device (3) adjacent the distal end (12) of a catheter (10) for guiding a boring tool (5) or other instrument into an occlusion (6) in a vessel (8), includes a guide element (30) adjacent the distal end (12). A penetrating element (33) having a first guide bore (38) terminating in a distal cutting edge (40) is rotatable in a second guide bore (45) extending through the guide element. External threads on the penetrating element (33) are engageable with internal threads in the second guide bore (45), so (Continued)

that by rotating the penetrating element (33) the distal cutting edge (40) is urged outwardly to penetrate the occlusion (6). With the penetrating element (33) securely engaged in the occlusion (6), a boring tool (5) and other instruments can then be sequentially guided through the catheter (10) and the first guide bore (38) directly into the occlusion.

21 Claims, 5 Drawing Sheets

(51) Int. Cl.
    *A61B 17/22*       (2006.01)
    *A61B 17/34*       (2006.01)
    *A61B 17/32*       (2006.01)
    *A61F 2/958*       (2013.01)

(52) U.S. Cl.
    CPC ............... *A61B 2017/22044* (2013.01); *A61B 2017/22069* (2013.01); *A61B 2017/22077* (2013.01); *A61B 2017/22094* (2013.01); *A61B 2017/22095* (2013.01); *A61B 2017/320052* (2013.01); *A61B 2017/3488* (2013.01); *A61F 2/958* (2013.01)

(58) Field of Classification Search
    CPC .......... A61B 2017/22094; A61B 2017/22095; A61B 2017/0424; A61B 2017/0425; A61B 2017/0432; A61B 2017/0433; A61F 9/00763
    See application file for complete search history.

(56) References Cited

U.S. PATENT DOCUMENTS

| | | | | |
|---|---|---|---|---|
| 5,776,142 | A * | 7/1998 | Gunderson | A61F 2/88 606/108 |
| 7,887,574 | B2 * | 2/2011 | McFerran | A61F 2/95 623/1.11 |
| 8,109,953 | B1 * | 2/2012 | King, III | A61B 17/22 606/159 |
| 8,133,243 | B2 * | 3/2012 | Lupton | A61B 17/3207 606/159 |
| 8,597,314 | B2 * | 12/2013 | McGhie | A61B 17/3207 606/159 |
| 10,136,914 | B2 * | 11/2018 | Lupton | A61B 17/3207 |
| 2008/0172008 | A1 * | 7/2008 | Root | A61M 25/0068 604/264 |
| 2009/0306597 | A1 * | 12/2009 | Lupton | A61B 17/3207 604/164.13 |
| 2011/0160755 | A1 * | 6/2011 | McGhie | A61B 17/3207 606/159 |
| 2011/0208222 | A1 * | 8/2011 | Ljahnicky | A61B 17/320758 606/159 |

OTHER PUBLICATIONS

Written Opinion for PCT/IE 2017/000003 dated May 4, 2017 [PCT/ISA/237].

\* cited by examiner

Fig. 12

DEVICE AND A METHOD FOR GUIDING A BORING TOOL, A GUIDE WIRE OR AN INSTRUMENT INTO ENGAGEMENT WITH AN OCCLUSION IN A VESSEL OR A WALL OF THE VESSEL IN THE BODY OF A HUMAN OR ANIMAL SUBJECT

The present invention relates to a device for guiding a guide wire, a boring tool, and/or an instrument into engagement with an occlusion in a vessel or a wall of the vessel or other part of the vessel in the body of a human or animal subject, and the invention also relates to a method for guiding a guide wire, a boring tool and/or an instrument into engagement with an occlusion in a vessel or a wall of the vessel or other part of the vessel in the body of a human or animal subject. This invention also relates to a catheter and a to balloon catheter comprising the device.

Devices for unblocking an occlusion in a remote vessel in the body of a human or animal subject or for use in the unblocking of such an occlusion are known, such devices are typically used for unblocking or for use in the unblocking of an occlusion in an artery or a vein, which may be a cardiovascular artery or vein or a peripheral blood vessel. However, it will be understood by those skilled in the art that such devices may be used for unblocking an occlusion in any vessel, be it remote or otherwise, or be it a blood vessel or otherwise, in the body of a human or animal subject. Such devices comprise a balloon catheter, and when the balloon is located in the occluded vessel the balloon is inflated for anchoring the distal end of the catheter in the vessel adjacent the occlusion. A boring tool or a guide wire is urged through the catheter of the balloon catheter and is guided by the anchored catheter into the occlusion. Such devices are disclosed in U.S. published Patent Application Specification No. 2009/0306597 and in PCT published Patent Application Specification No. WO 2012/123930. However, it has been found that when the boring tool or guide wire, having formed an opening through or into the occlusion, has been withdrawn from the occlusion, the distal end of the balloon catheter may slip out of alignment with the opening formed through or into the occlusion, thereby making it difficult if not impossible to direct other boring tools, guide wires, stent carriers or other instruments into the opening already formed through or into the occlusion.

There is therefore a need for a device for guiding a guide wire, a boring tool or an instrument into engagement with an occlusion in a vessel, a wall of a vessel or other part of a vessel in the body of a human or animal subject which addresses this problem, and there is also a need for a method for guiding a guide wire, a boring tool or a surgical instrument into engagement with an occlusion in a vessel, a wall of a vessel or other part of a vessel in the body of a human or animal subject which addressed this problem. The present invention is directed towards providing such a device and a method, and the invention is also directed towards providing a balloon catheter which comprises the device.

According to the invention there is provided a device for guiding one of a guide wire, a boring tool and an instrument into engagement with one of an occlusion in a vessel and a wall of a vessel, the device comprising a penetrating element extending between a proximal end and a distal end and terminating at the distal end in a distal cutting edge for cutting into the one of the occlusion and the wall of the vessel, and having a first guide bore extending therethrough for accommodating and guiding the one of the guide wire, the boring tool and the instrument into engagement with the one of the occlusion and the wall of the to vessel, and an external portion comprising an external screw thread, a guide element having a second guide bore extending therethrough for accommodating and guiding the penetrating element into engagement with the one of the occlusion and the wall of the vessel, at least a portion of the second guide bore comprising an internal screw thread for engaging and co-operating with the external screw thread of the penetrating element, the guide element being configured for anchoring in the vessel with a distal end of the second guide bore thereof adjacent the one of the occlusion and the wall of the vessel, so that with the guide element anchored in the vessel, by rotating the penetrating element in the second guide bore, the penetrating element is urged by the co-operating action of the external and internal screw threads into penetrating engagement with the one of the occlusion and the wall of the vessel.

Preferably, the penetrating element comprises an engagement means configured to engage an operating means for rotating the penetrating element in the second guide bore. Advantageously, the engagement means of the penetrating element comprises a releasable engagement means configured to releasably engage the operating means.

In one aspect of the invention the operating means for rotating the penetrating element in the second guide bore of the guide element is provided. Preferably, the operating means is releasably engageable with the engagement means of the penetrating element.

In one aspect of the invention the engagement means of the penetrating element comprises one of a pair of interengageable complementary formations and the other one of the pair of the interengageable complementary formations is located on the operating means. Preferably, the one of the interengageable complementary formations located on the operating means is located adjacent the distal end thereof.

In another aspect of the invention one of the interengageable complementary formations comprises at least one spade element, and the other one of the interengageable complementary formations comprises at least one engagement groove engageable with the corresponding spade element. Preferably, the engagement means of the penetrating element comprises the engagement groove of the pair of interengageable complementary formations. Advantageously, the engagement groove extends radially from and longitudinally into the penetrating element adjacent the proximal end thereof. Preferably, a pair of radially extending engagement grooves are provided, the radially extending engagement grooves extending radially from the first guide bore extending through the penetrating element on respective opposite sides thereof.

In one aspect of the invention the at least one spade element extends radially from the operating means for engaging a corresponding radially extending engagement groove in the penetrating element. Preferably, a pair of spade elements extend radially from the operating means on respective opposite sides thereof for engaging corresponding ones of the engagement grooves.

In another aspect of the invention the operating means comprises an elongated spigot extending longitudinally therefrom for engaging the first guide bore of the penetrating element for facilitating delivery of the penetrating element through the second guide bore of the guide element to the internal screw thread of the second guide bore. Preferably, the spade element extend on respective opposite sides of the spigot of the operating means.

In another aspect of the invention the distal cutting edge of the penetrating element extends around the first guide bore of the penetrating element. Preferably, the penetrating element comprises an elongated tubular element extending between the distal cutting edge and the proximal end thereof.

In one aspect of the invention the penetrating element is of length between the proximal end and the distal cutting edge thereof in the range of 5 mm to 60 mm. Preferably, the penetrating element is of length between the proximal end and the distal cutting edge thereof in the range of 10 mm to 40 mm. Advantageously, the penetrating element is of length between the proximal end and the distal cutting edge thereof of approximately 20 mm.

In another aspect of the invention the maximum outer transverse cross-sectional dimension of the penetrating element lies in the range of 0.28 mm to 0.76 mm. Preferably, the maximum outer transverse cross-sectional dimension of the penetrating element lies in the range of 0.40 mm to 0.60 mm. Advantageously, the maximum outer transverse cross-sectional dimension of the penetrating element is approximately 0.50 mm.

In one aspect of the invention the first guide bore is of circular transverse cross-section. Preferably, the distal cutting edge of the penetrating element is substantially circular.

In one aspect of the invention the penetrating element comprises a cylindrical wall and the external screw thread is located on the outer surface of the cylindrical wall.

In another aspect of the invention a limit means is provided on the penetrating element for limiting the travel of the penetrating element in a direction distally outwardly of the second guide bore of the guide element. Preferably, the limit means of the penetrating element comprises an unthreaded limit portion of the outer surface of the penetrating element proximal of the external screw thread thereof.

Advantageously, the unthreaded limit portion of the outer surface of the penetrating element is of diameter at least greater than the diameter of the root of the external screw thread thereof. Ideally, the unthreaded limit portion of the outer surface of the penetrating element is located adjacent the proximal end of the external screw thread on the penetrating element.

In another aspect of the invention one of the outer and inner surfaces of the wall of the penetrating element adjacent the distal end thereof converges distally towards the other one of the inner and outer surfaces of the wall of the penetrating element to define the distal cutting edge. Preferably, the outer surface of the wall of the penetrating element adjacent the distal end thereof converges towards the inner surface thereof to define the distal cutting edge. Alternatively, the inner and outer surfaces of the wall of the penetrating element adjacent the distal end thereof converge towards each other to define the distal cutting edge.

In one aspect of the invention the first guide bore of the penetrating element defines a first central guide axis, and the external screw thread of the penetrating element defines a first central thread axis. Preferably, the external screw thread of the penetrating element is configured so that the first central thread axis extends substantially parallel to the first central guide axis. Advantageously, the external screw thread of the penetrating element is configured so that the first central thread axis substantially coincides with the first central guide axis.

In another aspect of the invention the second guide bore of the guide element defines a second central guide axis, and the guide element defines a main central axis.

In a further aspect of the invention the guide element is configured for anchoring in the vessel with the second central guide axis of the second guide bore extending substantially parallel to the second central axis of the guide element. Preferably, the guide element is configured with the second central guide axis extending substantially parallel to the main central axis of the guide element. Advantageously, the guide element is configured with the second central guide axis substantially coinciding with the main central axis of the guide element.

In another aspect of the invention the guide element is configured with the second central guide axis of the guide element extending at an angle greater than zero to the main central axis thereof.

In another aspect of the invention the guide element is configured with the second central guide axis of the guide element configured to extend at an angle in the range of 5° to 90° to the main central axis of the guide element. Preferably, the guide element is configured with the second central guide axis of the guide element configured to extend at an angle in the range of 10° to 80° to the main central axis of the guide element. Advantageously, the guide element is configured with the second central guide axis of the guide element configured to extend at an angle in the range of 15° to 75° to the second central axis of the guide element. Ideally, the guide element is configured with the second central guide axis of the guide element configured to extend at an angle in the range of 20° to 70° to the main central axis of the guide element. Preferably, the guide element is configured with the second central guide axis of the guide element configured to extend at an angle in the range of 25° to 65° to the main central axis of the guide element. Advantageously, the guide element is configured with the second central guide axis of the guide element configured to extend at an angle in the range of 30° to 60° to the main central axis of the guide element.

Preferably, the guide element is configured with the second central guide axis of the guide element configured to extend at an angle in the range of 35° to 55° to the main central axis of the guide element. Advantageously, the guide element is configured with the second central guide axis of the guide element configured to extend at an angle in the range of 40° to 50° to the main central axis of the guide element. Ideally, the guide element is configured with the second central guide axis of the guide element configured to extend at an angle in the range of approximately 45° to the main central axis of the guide element.

In one aspect of the invention an internal screw thread is located in the first guide bore of the penetrating element configured to engage and co-operate with a corresponding external screw thread on one of a boring tool, a guide wire and an instrument.

In another aspect of the invention an anchoring means is provided for anchoring the guide element in a vessel. Preferably, the anchoring means comprises an expandable element expandable within the vessel. Advantageously, the expandable element comprises an inflatable balloon.

Preferably, the expandable element defines a longitudinally extending central axis, the central axis defined by the expandable element substantially coinciding with the main central axis of the guide element.

In another aspect of the invention the guide element is located adjacent a distal end of an elongated catheter. Preferably, the catheter defines an elongated main lumen extending longitudinally therethrough and communicating with the second guide bore of the guide element for accommodating the operating means to the penetrating element. Advantageously, the main lumen extending through the catheter is substantially aligned with the second guide accommodating bore of the guide element.

In another aspect of the invention the catheter comprises a balloon catheter, the element being located adjacent the distal end of a balloon catheter, and the balloon of the balloon catheter forming the anchor means of the guide element. Preferably, a portion of the main lumen of the catheter adjacent the balloon defines a main lumen central axis.

In one aspect of the invention the second central guide axis of the guide element extends substantially parallel to the main lumen central axis. Preferably, the second central guide axis of the guide element substantially coincides with the main lumen central axis.

Alternatively, the second central guide axis of the guide element extends at an angle greater than zero to the main lumen central axis.

Preferably, the second central guide axis of the guide element diverges distally from the main lumen central axis.

Advantageously, the second central guide axis of the guide element extends substantially perpendicularly from the main lumen central axis.

The invention also provides a balloon catheter comprising an elongated catheter extending between a to proximal end and a distal end and having an elongated main lumen extending longitudinally therethrough from the proximal end to the distal end, an inflatable balloon located on the catheter for anchoring the catheter in a vessel in a body of a human or animal subject, the catheter terminating adjacent the distal end thereof in the device according to the invention with at least a portion of the guide element of the device located within the balloon and a distal portion of the guide element extending from the balloon.

In one aspect of the invention the anchoring means for anchoring the guide element of the device comprises the balloon of the balloon catheter.

In another aspect of the invention the device extends distally from the catheter. Preferably, the main lumen extending through the catheter is substantially aligned with the second guide accommodating bore of the guide element. Advantageously, the main lumen is of transverse cross-sectional area for accommodating the penetrating element therethrough.

Advantageously, the main lumen is of transverse cross-sectional area for accommodating the operating means therethrough.

In one aspect of the invention a portion of the main lumen of the catheter adjacent the balloon defines a main lumen central axis.

In another aspect of the invention the second central guide axis of the guide element extends substantially parallel to the main lumen central axis. Preferably, the second central guide axis of the guide element substantially coincides with the main lumen central axis.

Alternatively, the second central guide axis of the guide element extends at an angle greater than zero to the main lumen central axis.

In one aspect of the invention the guide element is configured with the second central guide axis of the guide element extending at an angle in the range of 5° to 90° to the main lumen central axis of the guide element.

In another aspect of the invention the guide element is configured with the second central guide axis of the guide element configured to extend at an angle in the range of 15° to 75° to the second central axis of the guide element. Preferably, the guide element is configured with the second central guide axis of the guide element configured to extend at an angle in the range of 25° to 65° to the second central axis of the guide element. Advantageously, the guide element is configured with the second central guide axis of the guide element configured to extend at an angle in the range of 30° to 60° to the second central axis of the guide element. Ideally, the guide element is configured with the second central guide axis of the guide element configured to extend at an angle in the range of approximately 45° to the second central axis of the guide element.

In another aspect of the invention the second central guide axis of the guide element diverges distally from the main lumen central axis.

In another aspect of the invention the second central guide axis of the guide element extends substantially perpendicularly from the main lumen central axis.

In another aspect of the invention the operating means for rotating the penetrating element in the guide element is provided extending longitudinally through the main lumen extending through the catheter the operating means being releasably engageable with the penetrating element for rotating the penetrating element in the guide element to urge the penetrating element into engagement with the one of the occlusion and the wall of the vessel. Preferably, the operating means is of length to extend from the penetrating element through the main lumen of the catheter to extend outwardly of the catheter adjacent the proximal end thereof.

In one aspect of the invention the balloon is located adjacent the distal end of the catheter.

Preferably, the catheter extends through the balloon and defines with the balloon an annular hollow interior region for receiving an inflating medium. Preferably, an inflating lumen extends longitudinally through the catheter from the proximal end thereof and communicates with the hollow interior region of the balloon within the balloon.

The invention also provides a method for guiding one of a guide wire, a boring tool and an instrument into engagement with one of an occlusion in a vessel and a wall of the vessel in the body of a human or animal subject, the method comprising providing a penetrating element terminating in a distal cutting edge for cutting into and penetrating the one of the occlusion and the wall of the vessel, providing a first guide bore extending through the penetrating element for accommodating and guiding the one of the guide wire, the boring tool and the instrument into engagement with the one of the occlusion and the wall of the vessel, and providing an external screw thread on the penetrating element, locating the penetrating element in a second guide bore extending through a guide element and engaging the external screw thread of the penetrating element with internal screw thread in the second guide bore of the guide element, anchoring the guide element in the vessel with a distal end of the second guide bore of the guide element adjacent the one of the occlusion and the wall of the vessel, rotating the penetrating element in the second guide bore of the guide element for urging the penetrating element into penetrating engagement with the one of the occlusion and the wall of the vessel, and guiding the one of the guide wire, the boring tool and the instrument through the first guide bore of the penetrating element into engagement with the one of the occlusion and the wall of the vessel. Preferably, the penetrating element is rotated in the second guide bore of the guide element by an operating means engaged with the penetrating element adjacent the proximal end thereof. Advantageously, the operating means is releasably engaged with the penetrating element.

In one aspect of the invention the operating means is urged through the second guide bore in the guide element for engaging the penetrating element.

In another aspect of the invention an internal screw thread is provided in the first guide bore of the penetrating element for engaging and co-operating with a corresponding external screw thread on one of a boring tool, a guide wire and an instrument, and the one of the boring tool, the guide wire and the instrument is rotated in the first guide bore of the penetrating element with the external screw thread of the boring tool engaged with the internal screw thread in the first guide bore of the penetrating element for urging the boring tool through the first guide bore of the penetrating element.

In another aspect of the invention the guide element is anchored in the vessel by an expandable element engageable with the vessel. Preferably, the expandable element comprises an inflatable balloon. Advantageously, the expandable element comprises a balloon of a balloon catheter, the balloon being located on the distal end of the catheter for locating and anchoring the guide element in the vessel.

In another aspect of the invention the guide element extends distally from the distal end of the catheter.

Preferably, the guide element is formed by a distal portion of the catheter.

Advantageously, the guide element is located adjacent the distal end of the catheter with at least a portion of the guide element extending into the balloon, and a distal portion of the guide element extending from the balloon.

In another aspect of the invention the operating means is configured for delivering the penetrating element through a main lumen of the catheter and the second guide bore of the guide element to the internal screw thread of the second guide bore.

In a further aspect of the invention the balloon of the balloon catheter is urged into the vessel and is anchored in the vessel with the distal end of the guide element adjacent the occlusion or the wall of the vessel by inflating the balloon therein.

Preferably, travel of the penetrating element in a direction distally outwardly of the second guide bore of the guide element is limited by a limit means.

The advantages of the invention are many. A particularly important advantage of the invention is achieved by virtue of the fact that once the penetrating element is engaged in the occlusion or the wall of the vessel, a direct path from the second guide bore of the guide element, and in turn the first guide bore of the penetrating element into the opening or bore formed through or into the occlusion or wall of the vessel is continuously maintained by the penetrating element, since the penetrating element is in continuous engagement and alignment with the opening or bore in the occlusion or vessel wall. This, thereby allows boring tools, guide wires and other instruments to be replaced by other boring tools, guide wires and instruments without any danger of the first guide bore of the penetrating element going out of alignment with the opening or bore formed into or through the occlusion or vessel wall. This is a particularly important advantage where it is desired to locate, for example, a stent in an occlusion after a bore or opening has been formed through the occlusion in order to maintain the bore or opening through the occlusion open. In such cases, it is normal to form a bore or opening through the occlusion by one or more boring tools, and then subsequently place a stent in the bore by use of a stent delivery catheter. By virtue of the fact that the penetrating element continuously maintains a direct path into the bore formed through the occlusion after the boring tool has been removed, a guide wire can be passed through the first guide bore of the penetrating element directly into the bore or opening extending through the occlusion, and a stent delivery catheter can then be passed over the guide wire through the first guide bore of the penetrating element directly into the opening or bore extending through the occlusion for in turn placing the stent within the opening or bore extending through the occlusion.

The invention will be more clearly understood from the following description of some preferred embodiments thereof, which are given by way of example only, with reference to the accompanying drawings, in which.

Figure 6:
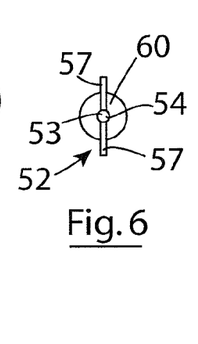
FIG. 6 is an end elevational view from one end of the portion of FIG. 5 of the device of the balloon catheter of FIG. 1.
Figure 7:
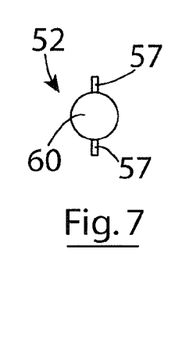
FIG. 7 is an end elevational view from the other end to that of FIG. 4 of the portion of FIG. 5 of the device of the balloon catheter of FIG. 1.
Figure 8:
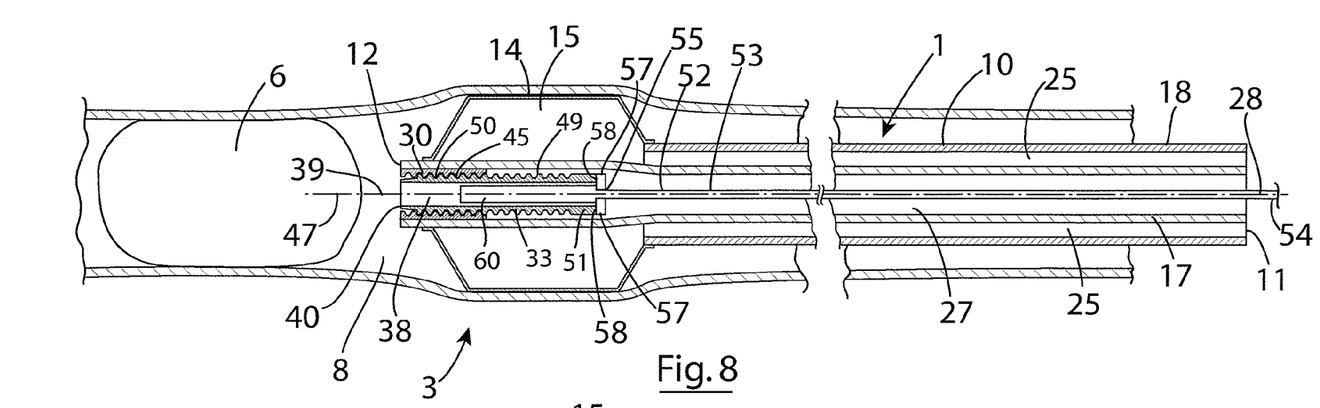
FIG. 8 is a cross-sectional side elevational view of the balloon catheter and the device of FIG. 1 in use.
Figure 9:
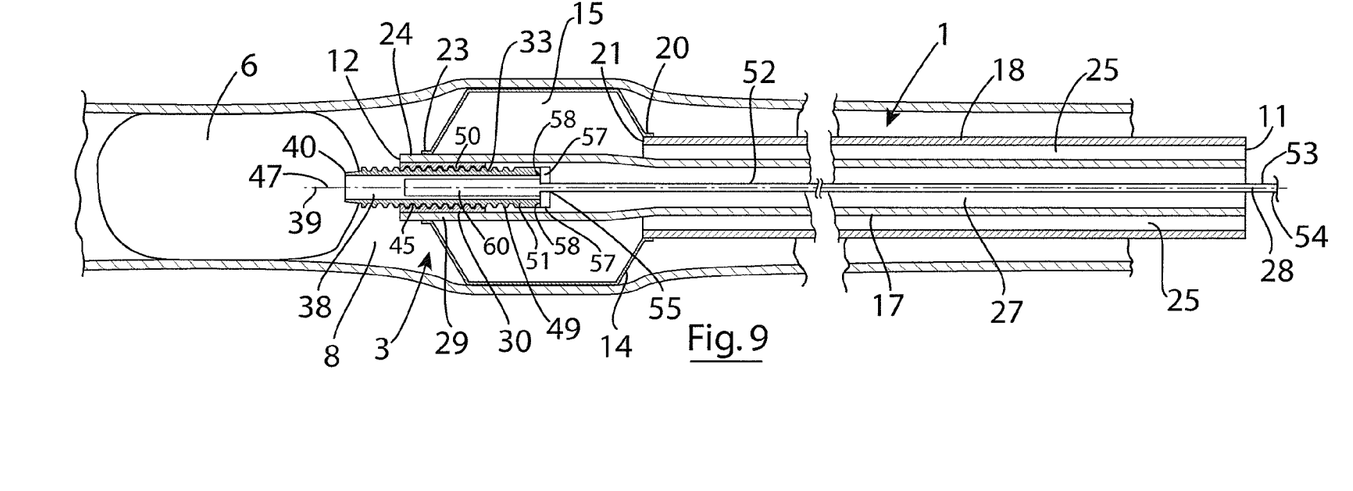
FIG. 9 is another cross-sectional side elevational view of the balloon catheter and the device of FIG. 1 in use.
Figure 10:
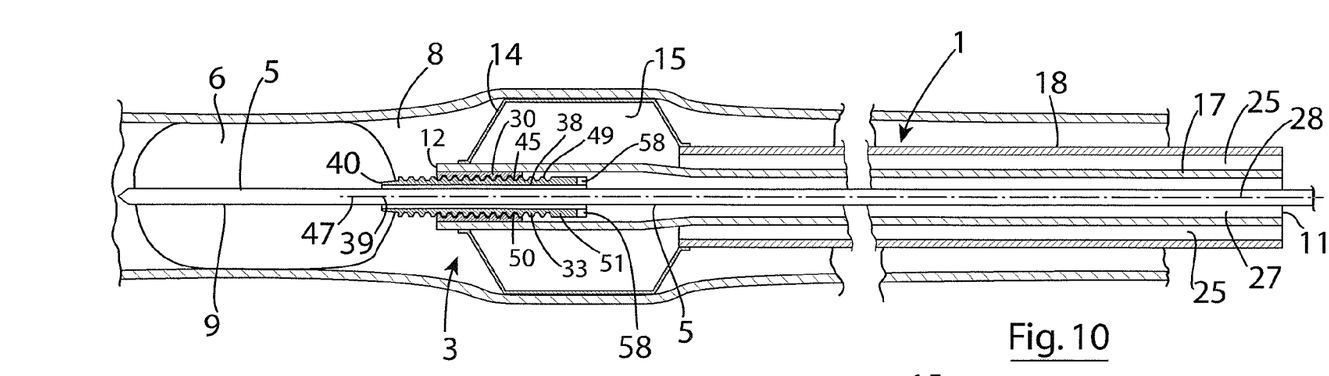
FIG. 10 is another cross-sectional side elevational view of the balloon catheter and the device of FIG. 1 illustrated in use.

Referring to the drawings, and initially to FIGS. 1 to 10 thereof, which are not to scale, there is illustrated a balloon catheter 1 according to the invention, indicated generally by the reference numeral 1, which comprises a device also according to the invention and indicated generally by the reference number 3 for guiding, for example, a boring tool 5 into engagement with, for example, an occlusion 6 in a remote vessel 8 in the body (not shown) of a human or animal subject, see FIGS. 8 to 10 for forming a bore 9 into or completely through the occlusion 6. The occlusion 6 in this embodiment of the invention is an occlusion formed by a build-up of plaque in the vessel 8, which in this case is a peripheral blood vessel, but may be an artery of the cardiovascular system of the subject. However, it will be readily apparent to those skilled in the art that the balloon catheter 1 and the device 3 may be used for guiding any surgical or other instrument into engagement with an occlusion, a wall of a vessel or any other part of a vessel to which it is required to guide one or more boring tools, instruments, guide wires or the like to a specific location in an occlusion or a wall of a vessel. The vessel may be remotely or otherwise located in the body of the human or animal subject.

Figure 1:
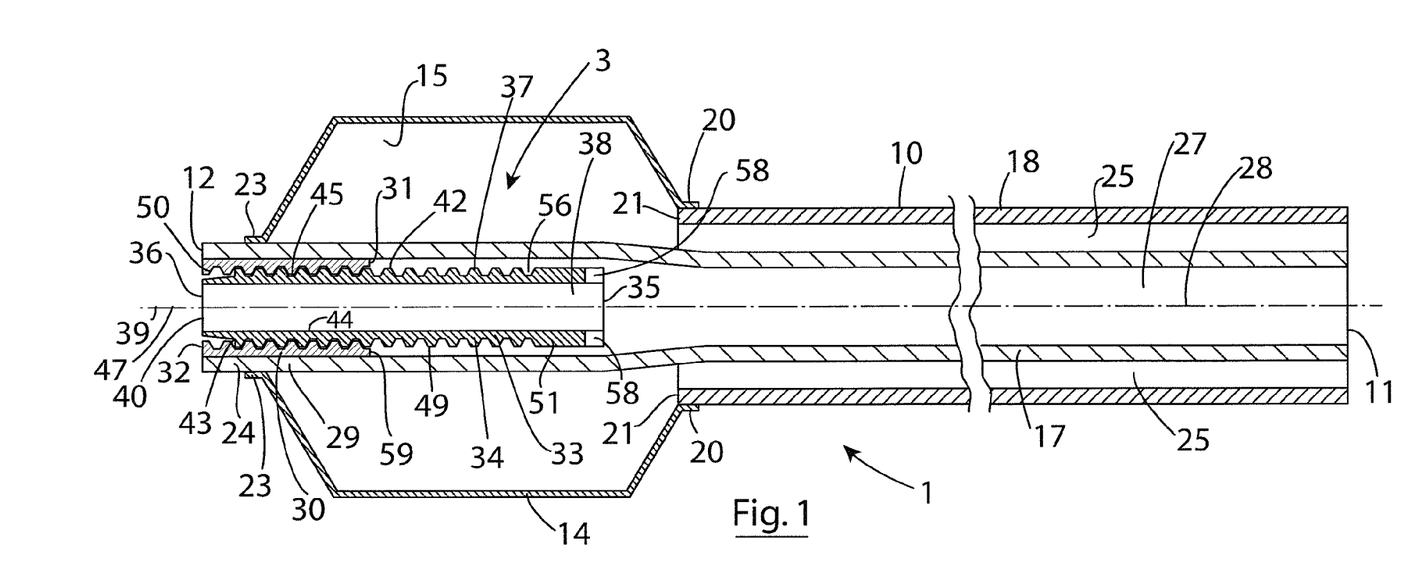
FIG. 1 is a cross-sectional side elevational view of a balloon catheter according to the invention comprising a device also according to the invention for guiding one of a boring tool, a guide wire and/or an instrument into an occlusion in a vessel.
Figure 2:
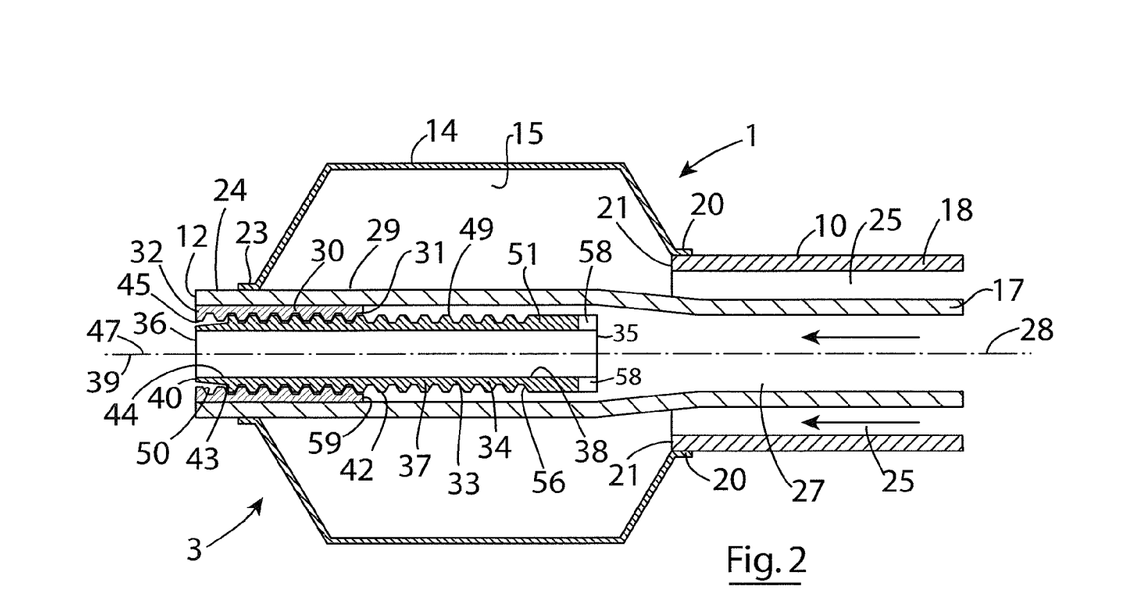
FIG. 2 is an enlarged cross-sectional side elevational view of a portion of the balloon catheter of FIG. 1.

The balloon catheter 1 comprising an elongated catheter 10 of circular transverse cross-section extending between a proximal end 11 and a distal end 12. The catheter 10 may be of any suitable material, and the material in some cases will be dependent on the location and type of vessel in which the occlusion is located. An anchoring means for anchoring the catheter 10 and in turn the device 3 in the vessel 8, in this embodiment of the invention, comprises an expandable element, namely, an inflatable balloon 14 located on the catheter 10 adjacent the distal end 12 thereof. The balloon 14 extends around the catheter 10 and defines with the catheter 10 an inflatable hollow interior region or annulus 15. The balloon 14 is of a flexible resilient material, and when inflated is substantially cylindrical, although it will be appreciated that when inflated in a vessel, the balloon 14 will tend to assume the shape of the vessel. In this embodiment of the invention the catheter 10 is formed by extrusion and comprises an inner tubular member 17 of circular transverse cross-section and an outer tubular member 18 also of circular transverse cross-section, which extends around and is coaxial with the inner tubular member 17. Longitudinally extending ribs (not shown) which are equi-spaced apart circumferentially around the inner tubular member 17 extend radially from the inner tubular member 17 to the outer tubular member 18 for retaining the inner and outer tubular members 17 and 18 spaced apart from each other and coaxially with each other.

A proximal end 20 of the balloon 14 is sealably secured to and around the outer tubular member 18 adjacent a distal end 21 thereof, and a distal end 23 of the balloon 14 is sealably secured to and around the inner tubular member 17 thereof adjacent a distal end 24 thereof so that the balloon 14 is sealably secured to the catheter 10. A plurality of inflating lumens 25 are formed between the inner and outer tubular members 17 and 18 by the ribs (not shown) and extend longitudinally through the catheter 10 from the proximal end 11 of the catheter 10 to the distal end 21 of the outer tubular member 18 and communicate with the inflatable annulus 15 of the balloon 14 for accommodating air or other suitable inflating medium, for example, a saline solution, for inflating the balloon 14. The inner tubular member 17 defines an elongated main lumen 27 of circular transverse cross-section, which extends longitudinally through the catheter 10 from the proximal end 11 to the distal end 12 thereof for accommodating the boring tool 5, a guide wire and/or other instruments for treating and/or opening the occlusion 6. The main lumen 27 defines a main lumen central axis 28.

A guide element 30 of circular transverse cross-section extending between a proximal end 31 and a distal end 32 is located and rigidly secured in the main lumen 27 adjacent the distal end 12 of the catheter 10. The distal end 32 of the guide element 30 substantially coincides with the distal end 12 of the catheter 10, and the guide element 30 extends into the main lumen 27 from the distal end 12 of the catheter 10, so that the majority of the guide element 30 is located within the balloon 14. The guide element 30 may be of a polymer material or of a suitable steel, for example, a stainless steel material. A cylindrical penetrating element 33 for engaging and penetrating into the occlusion 6 is urgeable through the main lumen 27 of the catheter 10 from the proximal end 11 thereof to the distal end 12 thereof as will be described in more detail below, and is urgeable through and from the distal end 32 of the guide element 30 into penetrating engagement with the occlusion 6, as will also be described below.

Figure 3:
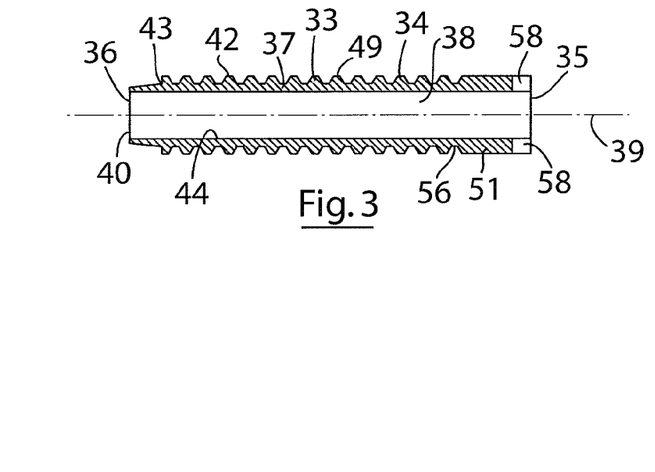
FIG. 3 is a cross-sectional side elevational view of a portion of the device of the balloon catheter of FIG. 1.
Figure 4:
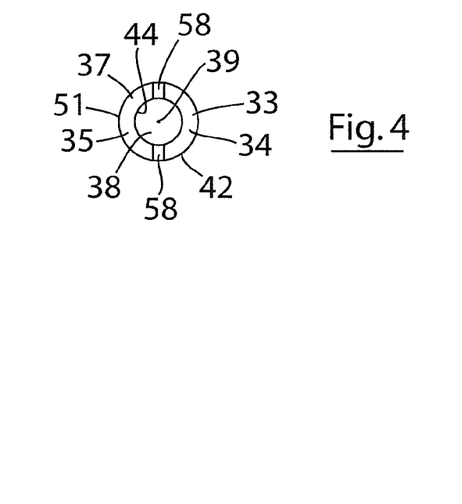
FIG. 4 is an end elevational view of the portion of FIG. 3 of the device of the balloon catheter of FIG. 1.

The penetrating element 33 comprises an elongated tubular member 34 of stainless steel material and of circular transverse cross-section extending between a proximal end 35 and a distal end 36. The tubular element 34 of the penetrating element 33 comprises a cylindrical wall 37 which defines a first guide bore 38 of circular transverse cross-section extending through the penetrating element 33 for accommodating the boring tool 5 therethrough and for guiding the boring tool 5 into the occlusion 6, as well as for accommodating and guiding guide wires and instruments into the occlusion 6. The first guide bore 38 defines a longitudinally extending first central guide axis 39 which coincides with the central geometric axis of the penetrating element 33.

The penetrating element 33 terminates at its distal end 36 in a distal cutting edge 40 which extends around the side wall 37 of the penetrating element 33 for penetrating into the occlusion 6. The cutting edge 40 is formed by tapering the outer cylindrical surface 42 of the side wall 37 adjacent the distal end 36 so that the outer surface 42 converges distally inwardly at 43 towards the inner surface 44 of the side wall 37, which forms the first guide bore 38, to form with the inner surface 44 the cutting edge 42 as a circular cutting edge 42 extending around the first guide bore 38 adjacent the distal end 36 of the penetrating element 33.

A second guide bore 45 of circular transverse cross-section extends axially through the guide element 30 for guiding the penetrating element 33 into engagement with the occlusion 6. The second guide bore 45 defines a second central guide axis 47, which in this embodiment of the invention coincides with the main lumen central axis 28.

External screw threads 49 are provided on the outer cylindrical surface 42 of the penetrating element 33 and are engageable with internal screw threads 50 formed in the guide element 30. Accordingly, by rotating the penetrating element 33 in the second guide bore 45 with the external screw threads 49 of the penetrating element 33 engaged and co-operating with the internal screw threads 50 of the second guide bore 45, the penetrating element 33 is urgeable inwardly and outwardly through the distal end 12 of the catheter 10.

A limit means for limiting the distance the penetrating element 33 can travel distally through the distal end 32 of the guide element 30 comprises an unthreaded limit portion 51 of the outer surface 42 of the penetrating element 33 located adjacent a proximal end 56 of the external screw threads 49 thereof. The unthreaded limit portion 51 of the penetrating element 33 is of diameter at least greater than the diameter of the root of the external screw threads 49, and in this case substantially similar to the maximum outer diameter of the external screw threads 49 of the penetrating element 33, so that when the unthreaded limit portion 51 of the penetrating element 33 abuts a proximal end 59 of the internal screw threads 50 further outward distal movement of the penetrating element 33 is prevented.

Figure 5:
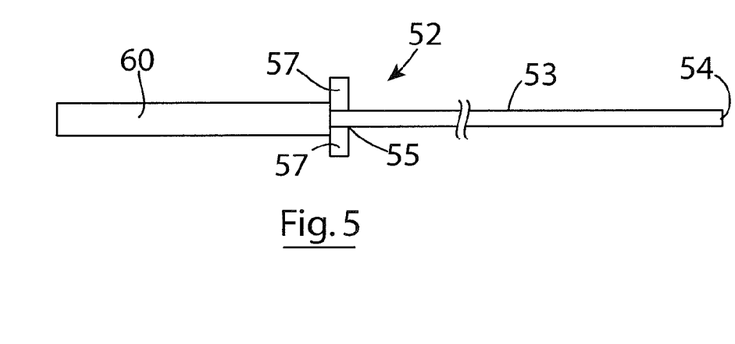
FIG. 5 is a side elevational view of another portion of the balloon catheter of FIG. 1.

An operating means, in this embodiment of the invention comprising an elongated operating member 52 is provided for rotating the penetrating element 33 in the second guide bore 45 for urging the penetrating element 33 inwardly and outwardly of the second guide bore 45. The operating member 52 is configured for extending into and through the main lumen 27 of the catheter 10 to the penetrating element 33. The operating member 52 comprises an elongated operating element 53 of the construction of a torsional guide wire and extends from a proximal end 54 to a distal end 55, and is configured to be rotatable in the main lumen 27, for in turn rotating the penetrating element 33. The distal end 55 of the operating element 53 terminates in one of a pair of interengageable complementary formations, one of which pair of interengageable complementary formations comprises a pair of spade elements 57 which extend distally longitudinally from and radially outwardly from the operating element 53. The spade elements 57 are configured for releasably engaging the other one of the pair of the interengageable complementary formations which in this embodiment of the invention is provided by an engagement means formed by a pair of engagement grooves 58 which extend longitudinally into the proximal end 35 of the penetrating element 33 and radially from the first guide bore 38 extending through the penetrating element 33 on respective opposite sides thereof.

The operating member 52 is also configured for delivering the penetrating element 33 through the main lumen 27 of the catheter 10 to the guide element 30 and into engagement with the internal screw threads 50 of the guide element 30, and in this embodiment of the invention the operating member 52 comprises an elongated spigot 60 of circular transverse cross-section extending distally longitudinally from the distal end 55 of the operating element 53. The spigot 60 is of diameter substantially similar to the diameter of the first guide bore 38 of the penetrating element 33, so that the spigot 60 is a relatively tight sliding fit in the first guide bore 38 of the penetrating element 33 for retaining the penetrating element 33 on the spigot 60 during delivery of the penetrating element 33 through the main lumen 27 of the catheter 10 to the guide element 30. The spade elements 57 extend radially from the spigot 60 on respective opposite sides thereof, so that when the spigot 60 is fully engaged in the first guide bore 38 of the penetrating element 33, the spade elements 57 engage with the corresponding engagement grooves 58 of the penetrating element 33.

The operating element 53 is of sufficient length to extend from the penetrating element 33 when the external screw threads 49 of the penetrating element 33 are engaged in the internal screw threads 50 of the guide element 30 with the unthreaded limit portion 51 of the penetrating element 33 in engagement with the proximal end 59 of the internal threads 50 of the guide element 30, to the proximal end 11 of the catheter 10 with the proximal end 54 of the operating element 53 extending outwardly of the proximal end 11 of the catheter 10, in order to facilitate gripping of the operating element 53 adjacent the proximal end 54 for rotating thereof, and in turn for rotating the penetrating element 33.

In this embodiment of the invention the length of the penetrating element 33 from the distal cutting edge 40 to the proximal end 35 is approximately 40 mm. The outer diameter of the penetrating element 33 is approximately 0.50 mm while the diameter of the first guide bore 38 extending through the penetrating element 33 is approximately 0.45 mm. However, it will be readily apparent to those skilled in the art that the penetrating element 33 may be of any suitable length outer diameter and internal diameter, and the dimensions of the penetrating element 33 will largely depend on the procedure with which it is being used, and for example, the length of the penetrating element 33 from the distal cutting edge 40 to the proximal end 35 may range from as low as 5 mm to as high as 60 mm, while the outer diameter of the penetrating element 33 may range from 0.28 mm to 0.76 mm, and the diameter of the first guide bore 38 of the penetrating element 33 may range from 0.229 mm to 0.71 mm.

Additionally, in this embodiment of the invention the guide element 30 is of length from the proximal end 31 to the distal end 32 approximately 15 mm, and the outer diameter of the guide element 30 is of length approximately 0.55 mm, while the diameter of the second guide bore 45 is approximately 0.50 mm. However, like the penetrating element 33, these dimensions of the guide element 30 will vary depending on the procedure with which the device is being used. In general, it is expected that the length of the guide element 30 from the proximal end 31 to the distal end 32 may range from 5 mm to 40 mm, while the outer diameter of the guide element 30 may range from 0.33 mm to 0.81 mm, and the diameter of the second guide bore 45 may range from 0.28 mm to 0.76 mm.

In use, to unblock an occlusion 6 in a vessel 8 of the cardiovascular system of the subject, a standard guide wire of the type which will be well known to those skilled in the art is entered into the arterial system of a subject, typically through the femoral artery and is urged from the femoral artery through the arterial system of the body of the subject and eventually into the vessel 8 in which the occlusion 6 is located. The insertion and guiding of such a guide wire to an occlusion in a vessel of the cardiovascular system of a subject will be well known to those skilled in the art. When the guide wire has been guided to the occlusion 6 in the vessel 8, the balloon catheter 1 with the balloon 14 deflated is then urged over the guide wire through the arterial system of the subject until the distal end 12 of the catheter 10 and the balloon 14 are located in the vessel 8 adjacent the occlusion 6.

The balloon 14 is then inflated in the vessel 8 for anchoring the catheter 10 in the vessel 8 with the distal end 12 of the catheter 10 located adjacent the occlusion 6, and substantially centrally aligned with the occlusion 6. The balloon 14 is inflated by delivering a suitable inflating medium, for example, air, a saline solution or the like through the inflating lumens 25 of the catheter 10 into annulus 15 of the balloon 14. With the balloon 14 inflated and rigidly anchored in the vessel 8 and with the distal end 12 of the catheter 10 adjacent the occlusion 6, the guide wire is then removed from the catheter 10.

The penetrating element 33 is mounted on the spigot 60 of the operating member 52 with the spigot 60 engaged in the first guide bore 38 of the penetrating element 33. The penetrating element 33 is then delivered through the main lumen 27 of the catheter 10 by the operating member 52 until the external screw threads 49 of the penetrating element 33 engage the internal screw threads 50 of the guide element 30. If the spade elements 57 of the operating member 52 are not engaged in the engagement grooves 58 of the penetrating element 33, the operating member 52 is rotated and urged towards the penetrating element 33 until the spade elements 57 engage the engagement grooves 58.

Further rotation of the operating member 52 in a clockwise direction, assuming the external screw threads 49 of the penetrating element 33 and the internal threads 50 of the guide element 30 are right-hand threads, urges the penetrating element 33 outwardly through the distal end 32 of the guide element 30. Rotation of the penetrating element 33 by the operating member 52 is continued until the distal cutting edge 40 of the penetrating element 33 engages and penetrates into the occlusion 6, so that the penetrating element 33 is in tight secure penetrating engagement with the occlusion 6. By virtue of the fact that the distal end 12 of the catheter 10 is rigidly anchored in the vessel 8 by the balloon 14, as the penetrating element 33 is being rotated, the penetrating element 33 is urged outwardly through the distal end 32 of the guide element 30 against the anchoring action of the balloon 14 into the occlusion 6 with the distal cutting edge 40 of the penetrating element 32 cutting into the occlusion 6 in order to securely engage the occlusion 6.

When the penetrating element 33 is in secure penetrating engagement with the occlusion 6, the operating member 52 is withdrawn through the main lumen 27. The boring tool 5 is then urged through the main lumen 27 of the catheter 10 and in turn through the first guide bore 38 of the penetrating element 33 which guides the boring tool 5 directly into the occlusion 6 for boring through the occlusion 6 and opening a channel 9 through the occlusion 6. On removal of the boring tool 6, further boring tools and/or other instruments may be passed through the main lumen 27 of the catheter 10 and in turn through the first guide bore 38 of the penetrating element 33 and guided by the first guide bore 38 directly into the already opened channel through the occlusion 6 for enlarging the channel through the occlusion 6 or for carrying out further procedures.

Once a channel has been opened through the occlusion 6 to the desired cross-section, the boring tool 5 and/or other boring tools are removed through the main lumen 27. If desired a stent may be delivered through the main lumen 27 of the catheter 10 through the first guide bore 38 in the penetrating element 33 and in turn into the channel which has been opened through the occlusion 6. Typically, a stent would be delivered to the channel through the occlusion 6 with the stent in a collapsed state carried on a balloon of a stent delivery balloon catheter. The stent delivery balloon catheter with the stent in the collapsed state on the deflated balloon of the balloon catheter would be urged through the main lumen 27 of the catheter 10 and in turn through the first guide bore 38 of the penetrating element 33 until the stent was located in the channel through the occlusion 6. The balloon of the stent delivery balloon catheter is then inflated to expand the stent into engagement with the channel formed through the occlusion 6 and for further opening the channel and for retaining and maintaining the channel extending through the occlusion 6.

On completion of the location of a stent in a channel through the occlusion 6, the balloon or the stent delivery balloon catheter is deflated and the stent delivery balloon catheter is removed through the main lumen 27 of the catheter 10. The operating member 52 is then again urged through the main lumen 27 of the catheter 10 until the spigot 60 engages the first guide bore 38 extending through the penetrating element 33 and the spade elements 57 engage in the engagement grooves 58 of the penetrating element 33. The operating element 52 is then rotated in an anticlockwise direction for withdrawing the penetrating element 33 from the occlusion 6 and into the guide element 30. The balloon 14 of the balloon catheter 1 is deflated, and the balloon catheter 1 with the penetrating element 33 withdrawn into the guide element 30 and the operating member 52 are then removed through the arterial system of the subject.

Figure 11:
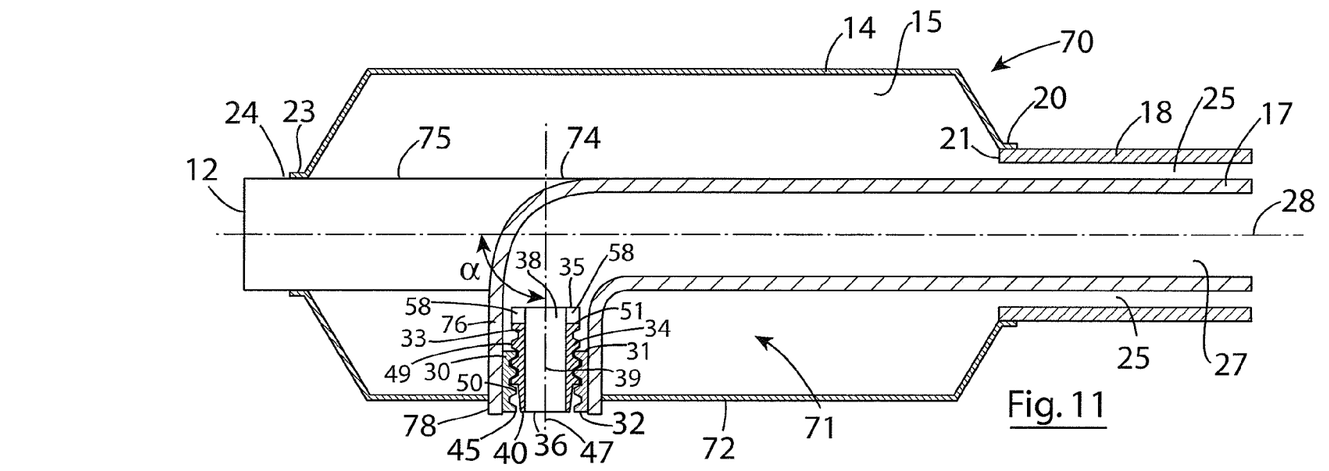
FIG. 11 is a view similar to FIG. 2 of a portion of a balloon catheter according to another embodiment of the invention comprising a device also according to the invention for guiding one of a boring tool, a guide wire and/or an instrument into a wall of a vessel or an occlusion in a branched vessel extending sidewardly from a vessel in which the device is anchored.

Referring now to FIG. 11 which is not to scale, there is illustrated a balloon catheter according to another embodiment of the invention indicated generally by the reference numeral 70, which also comprises a device also according to the invention and indicated generally by the reference numeral 71 for guiding one of a boring tool, a guide wire and/or an instrument into an occlusion in a vessel, or into a wall of a vessel. The balloon catheter 70 and the device 71 are substantially similar to the balloon catheter 1 and the device 3, respectively, described with reference to FIGS. 1 to 10, and similar components are identified by the same reference numerals. The only difference between the balloon catheter 70 and the device 71 on the one hand, and the balloon catheter 1 and the device 3 on the other hand, is that the device 70 extends from the catheter 10 within the balloon 14 at an angle α and extends through a cylindrical portion 72 of the balloon 14. The balloon catheter 70 and the device 71 is particularly suitable for guiding a boring tool, a guide wire or other instrument into a wall of a vessel, or into an occlusion in a vessel branched from a vessel in which the balloon 14 of the balloon catheter 70 is located.

In this embodiment of the invention the inner tubular member 17 of the catheter 10 is branched at 74 within the balloon 14. One portion 75 of the inner tubular member 17 is aligned with the remainder of the inner tubular portion 17 and extends through the balloon 14 to the distal end 23 of the balloon 14. The other branch 76 of the inner tubular member 17 extends at the angle α to the branch 75, and in turn the remainder of the inner tubular element 17, and a distal end 78 of the branch 76 extends through the cylindrical portion 72 of the balloon 14. In this embodiment of the invention the main lumen 27 extends through the inner tubular member 17 to the location 74 at which the inner tubular member 17 is branched, and in turn continues through the branch 76 of the inner tubular member 17. The guide element 30 is tightly and securely located in the branch 76 of the inner tubular member 17 with the distal end 32 of the guide element 30 terminating adjacent the distal end 78 of the branch 76. In this embodiment of the invention the second central guide axis 47 defined by the second guide bore 45 of the guide element 30 extends at the angle α to the main lumen central axis 28 of the catheter 10 adjacent the balloon 14. The angle α defined between the second central guide axis 47 and the main lumen central axis 28 may be of any value greater than 0° and just less than 180° and will depend on the application for which the balloon catheter 70 is required. In cases where the penetrating element 33 is to guide a boring tool or other instrument into a side wall of a vessel in which the balloon 14 is located perpendicularly to the side wall of the vessel, typically, the angle α defined between the second central guide axis 47 and the main lumen central axis 28 of the catheter 10 would be approximately 90° as illustrated in FIG. 11. However, if it were desired to guide a boring tool or other instrument into a side wall of a vessel at an angle less than or greater than 90° the angle α defined between the second central guide axis 47 and the main lumen central axis 28 of the catheter 10 would be set at an appropriate angle for guiding the boring tool or instrument into the wall of the vessel at the desired angle. Similarly, in cases where the balloon catheter 70 is required to guide a boring tool or other instrument into an occlusion in a vessel branched from the vessel in which the balloon 14 of the balloon catheter 70 is located, the branch portion 76 would extend from the inner tubular member 17 of the catheter 10 with the angle α defined between the second central guide axis 47 and the main central axis 28 of the catheter 10 being substantially similar to the angle at which the vessel with the occlusion therein extends from the vessel within which the balloon 14 of the balloon catheter 70 is located.

In this embodiment of the invention the guide element 30 is of length between its proximal end 31 and its distal end 32 of approximately 5 mm, and the length of the penetrating element 33 between its proximal end 35 and its distal end 36 is approximately 20 mm, although FIG. 11 is not to scale.

Otherwise, the balloon catheter 70 and the device 71 are similar to the balloon catheter 1 and the device 3, respectively.

In use the balloon catheter 70 is urged through the arterial system of a subject until the balloon 14 of the balloon catheter 70 is located in the appropriate vessel, and the balloon catheter 70 is orientated in the vessel until the distal end 78 of the branch 76 of the inner tubular member 17 is aligned with the location in the wall of the vessel into which a bore is to be formed or until the distal end 78 of the branch 76 of the inner tubular member 17 is aligned with the branched vessel in which the occlusion to be bored is located. Once the distal end 78 of the branch 76 of the inner tubular member 17 is aligned with the appropriate area of the vessel wall or an occlusion in a branched vessel, the balloon 14 is then inflated, and with the operating member 52 the penetrating element 33 is rotated with the external threads 49 of the penetrating element 33 engaging the internal threads 50 of the guide element 30 for urging the distal cutting edge 40 of the penetrating element 33 into penetrating engagement with the wall of the vessel or the occlusion in the branched vessel as the case may be. Thereafter operating and use of the balloon catheter 70 and the device 71 is similar to that already described with reference to the balloon catheter 1 and the device 3 thereof.

Figure 12:
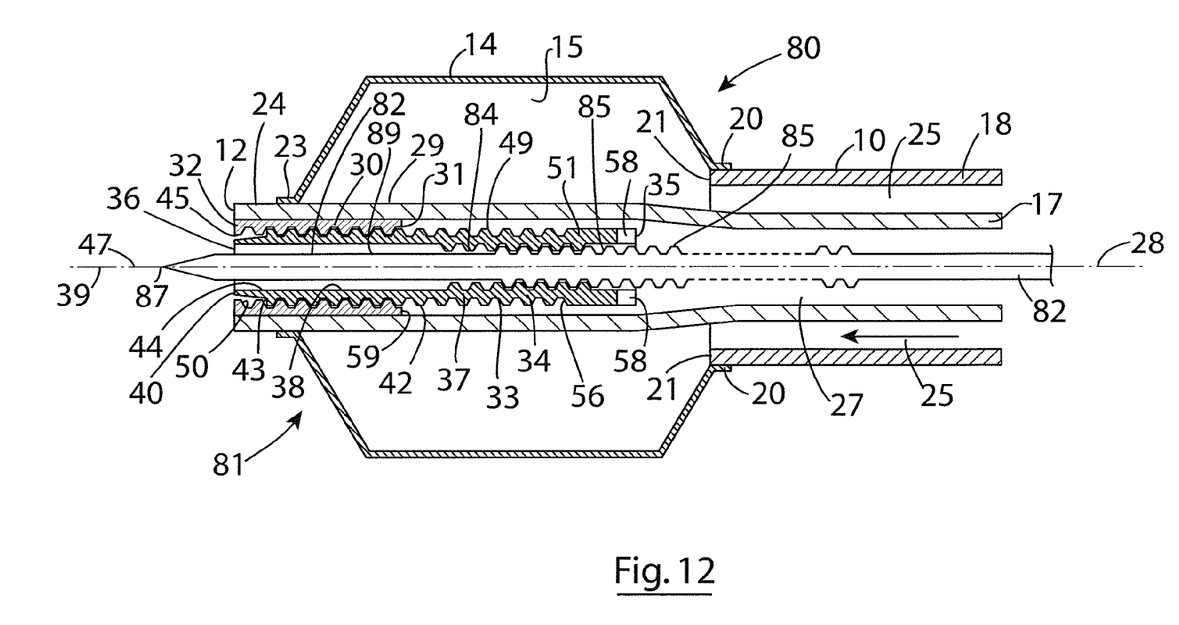
FIG. 12 is a view similar to FIG. 2 of a portion of a balloon catheter according to another embodiment of the invention comprising a device also according to another embodiment of the invention for guiding one of a boring tool, guide wire and an instrument into a wall of a vessel or an occlusion in a vessel in which the device is anchored.

Referring now to FIG. 12, which is not to scale, there is illustrated a balloon catheter according to another embodiment of the invention indicated generally by the reference numeral 80, which also comprises a device also according to the invention indicated generally by the reference numeral 81 for guiding one of a boring tool, a guide wire, and an instrument into an occlusion in a vessel or into a wall of a vessel. In this embodiment of the invention the device 81 is illustrated for guiding a boring tool 82 into an occlusion in a vessel. The balloon catheter 80 is substantially similar to the balloon catheter 1 and similar components are identified by the same reference numerals. Additionally, the device 81 is also substantially similar to the device 3, and similar components are also identified by the same reference numerals.

The main difference between the balloon catheter 80 and the balloon catheter 1 is that the penetrating element 33 as well as being provided with external screw threads 49 for engaging the internal screw threads 50 of the guide element 30, is also provided with internal screw threads 84 located in the first guide bore 38 of the penetrating element 33 for engaging corresponding external screw threads 85 on the boring tool 82. The provision of the internal screw threads 84 in the first guide bore 38 of the penetrating element 33 permits the boring tool 82 to be urged out of the penetrating element 33 and into an occlusion in a vessel by rotating the boring tool 82 in the first guide bore 38 of the penetrating element 33. In this embodiment of the invention the boring tool 82 terminates in a penetrating point 87 for penetrating into the occlusion, so that as the boring tool 82 is urged through the first guide bore 38 by rotation of the boring tool 82 in the penetrating element 33, the penetrating point 87 is urged into and through the occlusion.

In this embodiment of the invention the internal screw threads 84 in the first guide bore 38 of the penetrating element 33 are located towards the proximal end of the first guide bore 38, however, it will be readily apparent to those skilled in the art that if desired the internal screw threads 84 may extend throughout the full length of the first guide bore 38. The external screw threads 85 on the boring tool 82 may extend over only a short length of the boring tool, or over a longer length. The length which the external screw threads 85 extend along the boring tool 82, will largely be determined by the distance through which the boring tool 82 is to be urged outwardly of the penetrating element 33, and will also be dependent on the length of the internal screw threads 84 in the first guide bore 38 of the penetrating element 33. However, in general, it is envisaged that a reasonable length of the distal portion 89 of the boring tool 82 will be provided free of the external screw threads 85 so that the boring tool 82 will be able to penetrate through the full length of an occlusion without the external screw threads 85 engaging the occlusion.

The boring tool 82 as will be understood by those skilled in the art is secured to and extends from the distal end of an elongated carrier element, typically, an elongated torsional guide wire which is configured to extend from the boring tool 82 through the catheter 10 of the balloon catheter 80 to the proximal end 11 thereof and outwardly of the catheter 10 from the proximal end 11 thereof to permit manual rotation of the proximal end of the torsional guide wire for rotating the boring tool 82 within the first guide bore 38 of the penetrating element 33.

In use the penetrating element 33 is initially engaged with the occlusion through which a channel is to be formed therethrough, in a similar manner as already described with reference to the balloon catheter 1 and the device 3 with reference to FIGS. 1 to 10. Once the penetrating element 33 has been engaged in the occlusion, the operating member 52 is removed through the catheter 10. The boring tool 82 is then introduced into the main lumen 27 of the catheter 10 at the proximal end 11 thereof. The boring tool 82 is then urged through the main lumen 27 and in turn into the first guide bore 38 of the penetrating element 33 by the torsional guide wire, until the external screw threads 85 of the boring tool 82 engage the internal screw threads 84 of the penetrating element 33.

The boring tool 82 is then rotated in the first guide bore 38 of the penetrating element 33 by rotating the torsional guide wire to which the boring tool 82 is attached for urging the boring tool 82 through the first guide bore 38 of the penetrating element 33, and in turn directly into the occlusion from the first guide bore 38. Assuming that the internal and external screw threads 84 and 85 are right hand threads, the boring tool 82 is rotated in a clockwise direction for in turn urging the boring tool 82 into the occlusion. Thus, in this embodiment of the invention the penetrating element 33 guides the boring tool 82 directly into the occlusion, and furthermore the boring tool 82 is urged into the occlusion by the co-operating action of the internal and external screw threads 84 and 85 as the boring tool 82 is rotated in the first guide bore 38 of the penetrating element 33, so that the boring tool 82 is urged into and through the occlusion against the anchoring action of the balloon 14 in the vessel.

Otherwise, the balloon catheter 80 and the device 81 are similar to the balloon catheter 1 and the device 3 described with reference to FIGS. 1 to 10, and their operation is likewise similar.

A particularly important advantage of the balloon catheter 80 and the device 81 is that as well as the penetrating element 33 being urged into penetrating engagement with the occlusion by the penetrating element being urged against the anchoring action of the balloon 14 of the balloon catheter 80 which is anchored in the vessel, the boring tool 82 is also urged into the occlusion against the anchoring action of the balloon 14.

It is envisaged that instead of the boring tool 82 being secured to the distal end of a guide wire, the boring tool 82 could be provided with an engagement means at a proximal end thereof, which would be engageable by an operating member somewhat similar to the operating member 52 for rotating the boring tool 82 in the first guide bore 38 of the penetrating element 33. For example, it is envisaged that the boring tool 82 may be provided with a transversely extending engagement slot at its proximal end for engaging a spade element on the end of a torsional guide wire for rotating the boring tool 82 in the first guide bore 38 of the penetrating element 33. It is also envisaged that the in such a case, a stop means may be provided on the proximal end of the boring tool 82 in order to prevent the boring tool 82 passing completely through the first guide bore 38 of the penetrating element 33 through the distal end 36 of the penetrating element 33. It is envisaged that such a stop means would be located on the boring tool 82, and would be substantially similar to the enlarged portion 51 of enlarged diameter of the penetrating element 33, and the enlarged portion of enlarged diameter of the boring tool 82 would be located adjacent a proximal end of the external screw threads 85 of the boring tool 82 and would engage the proximal end of the internal screw threads 84 in the first guide bore 38 to prevent further movement of the boring tool 82 through the first guide bore 38 of the penetrating element 33 towards the distal end 36 thereof.

While particular constructions of balloon catheters have been described, any other suitable construction of balloon catheter may be used. It will be appreciated that while the interengageable complementary formations which provide for releasable engagement of the operating member 52 with the penetrating element 33 have been described as comprising a pair of spade elements extending from the operating member 52 which are engageable with corresponding radial engagement grooves in the penetrating element, any other suitable pair of interengageable complementary formations may be provided. It will also of course be appreciated that the engagement grooves may be provided on the operating member while the spade elements would be provided on the penetrating element.

While the penetrating element has been described as comprising a circular cutting edge formed by tapering the outer cylindrical surface of the penetrating element distally inwardly to form the cutting edge with the inner surface of the first guide bore extending through the penetrating element, it will be appreciated that the cutting edge may be formed by diverging the inner surface of the first guide bore of the penetrating element distally to the cylindrical outer surface of the penetrating element to form the circular cutting edge adjacent the distal end of the penetrating element. It will also be appreciated that the cutting edge may be defined by tapering the outer cylindrical surface of the penetrating element distally inwardly and also diverging the inner surface of the bore extending through the penetrating element outwardly to form the cutting edge between the tapering and diverging surfaces of the penetrating element.

It is also envisaged that the cutting edge instead of being formed by a smooth knife type cutting edge, could be formed by a serrated type cutting edge.

While the devices according to the invention have been described as comprising a guide element located in a main lumen of a balloon catheter adjacent the distal end of the catheter, it is envisaged that the guide element may be integral with the catheter of the balloon catheter, in which case the internal threads would be formed in the main lumen adjacent the distal end of the catheter.

It is also envisaged that the guide element could be provided as a separate element, and would be adapted for mounting on or coupling to the distal end of a balloon catheter with the second guide bore aligned with and communicating with the distal end of the main lumen of the balloon catheter. A proximal portion of the guide element could be adapted for releasably coupling to the balloon catheter whereby the proximal portion of the guide element would be configured to releasably grip a distal portion of the catheter of the balloon catheter, or would be releasably engageable with the balloon of the balloon catheter, and would be configured to expand with the balloon of the balloon catheter as the balloon of the balloon catheter is inflated.

Indeed, it is envisaged in certain embodiments of the invention that the second guide bore extending through the guide element need not necessarily be coaxial with the penetrating element, in other words, the second central axis defined by the second guide bore could be offset relative to the main central axis of the catheter, but in general would extend parallel to the central axis of the penetrating element.

While the devices has been described for use in unblocking an occlusion in a peripheral blood vessel, it will be readily apparent to those skilled in the art that the device may be used for unblocking any occlusion in any vessel, be it an arterial or venal vessel of a subject, cardiovascular vessel or any other vessel of the subject. Additionally, it is envisaged that while the devices have been described for guiding a boring tool into engagement with an occlusion, it will be readily apparent to those skilled in the art that the devices according to the invention may be used for guiding any element into engagement with an occlusion, for example, any surgical instrument, a guide wire or any other such instrument. It will also be appreciated that the devices according to the invention may be used for guiding an instrument, a guide wire, a boring tool or the like into engagement with a wall of a vessel or indeed any other part of a vessel whereby the penetrating element would be initially urged into penetrating engagement with the wall of the vessel or other part of the vessel, and the surgical instruments, boring tools, guide wires and the like would then be guided into the wall of the vessel or other part of the vessel through the first guide bore extending through the penetrating element which would be in penetrating engagement with the wall of the vessel or other part thereof.

While some of the elements of the balloon catheters and the devices according to the invention have been described as being of specific materials, it will be readily apparent to those skilled in the art that other suitable materials may be used. It will also be appreciated that while the penetrating element and the guide element of the balloon catheters and the devices have been described as being of specific dimensions, it will be readily apparent to those skilled in the art that the dimensions of the penetrating element and the guide element, and indeed any other elements of the balloon catheter and the device will largely be dependent on the application for which the balloon catheter and the device are to be used.

The invention claimed is:

1. A device for guiding one of a guide wire, a boring tool and an instrument into engagement with one of an occlusion in a vessel and a wall of a vessel, the device comprising a penetrating element extending between a proximal end and a distal end and terminating at the distal end in a distal cutting edge for cutting into the one of the occlusion and the wall of the vessel, and having a first guide bore extending therethrough for accommodating and guiding the one of the guide wire, the boring tool and the instrument into engagement with the one of the occlusion and the wall of the vessel, and an external portion comprising an external screw thread, a guide element having a second guide bore extending therethrough for accommodating and guiding the penetrating element into engagement with the one of the occlusion and the wall of the vessel, at least a portion of the second guide bore comprising an internal screw thread for engaging and co-operating with the external screw thread of the penetrating element, the guide element being configured for anchoring in the vessel with a distal end of the second guide bore thereof adjacent the one of the occlusion and the wall of the vessel, wherein the penetrating element comprises an engagement means configured to engage an operating means for rotating the penetrating element in the second guide bore, so that with the guide element anchored in the vessel, by rotating the penetrating element in the second guide bore, the penetrating element is urged by the co-operating action of the external and internal screw threads into penetrating engagement with the one of the occlusion and the wall of the vessel.

2. A device as claimed in claim 1 in which the engagement means of the penetrating element comprises a releasable engagement means configured to releasably engage the operating means.

3. A device as claimed in claim 1 further comprising the operating means for rotating the penetrating element in the second guide bore of the guide element.

4. A device as claimed in claim 3 in which the operating means comprises an elongated spigot extending longitudinally therefrom for engaging the first guide bore of the penetrating element for facilitating delivery of the penetrating element through the second guide bore of the guide element to the internal screw thread of the second guide bore.

5. A device as claimed in claim 3 in which the engagement means of the penetrating element comprises one of a pair of interengageable complementary formations, and the other one of the pair of the interengageable complementary formations is located on the operating means.

6. A device as claimed in claim 5 in which one of the interengageable complementary formations comprises at least one spade element, and the other one of the interengageable complementary formations comprises at least one engagement groove engageable with the corresponding spade element.

7. A device as claimed in claim 6 in which the at least one engagement groove is provided on the penetrating element and extends radially from and longitudinally into the penetrating element adjacent the proximal end thereof, and the at least one spade element extends radially from the operating means for engaging a corresponding one of the engagement grooves in the penetrating element.

8. A device as claimed in claim 7 in which a pair of the engagement grooves extend radially from the first guide bore extending through the penetrating element on respective opposite sides thereof, and a pair of the spade elements extend radially from the operating means on respective opposite sides thereof for engaging the corresponding ones of the engagement grooves.

9. A device as claimed in claim 1 in which a limit means is provided on the penetrating element for limiting the travel of the penetrating element in a direction distally outwardly of the second guide bore of the guide element.

10. A device as claimed in claim 1 in which the first guide bore of the penetrating element defines a first central guide axis, the external screw thread of the penetrating element defines a first central thread axis, the second guide bore of the guide element defines a second central guide axis, and the guide element defines a main central axis.

11. A device as claimed in claim 10 in which the guide element is configured for anchoring in the vessel with the second central guide axis of the second guide bore one of extending substantially parallel to the main central axis of the guide element, substantially coinciding with the main central axis of the guide element, and extending at an angle greater than zero to the main central axis of the guide element.

12. A device as claimed in claim 1 in which an internal screw thread is located in the first guide bore of the penetrating element configured to engage and co-operate with a corresponding external screw thread on one of a boring tool, a guide wire and an instrument.

13. A device as claimed in claim 1 in which an anchoring means is provided for anchoring the guide element in a vessel.

14. A device as claimed in claim 1 in which the guide element is located adjacent a distal end of an elongated catheter, the catheter defining an elongated main lumen extending longitudinally therethrough and communicating with the second guide bore of the guide element for accommodating the operating means to the penetrating element.

15. A balloon catheter comprising an elongated catheter extending between a proximal end and a distal end and having an elongated main lumen extending longitudinally therethrough from the proximal end to the distal end, an inflatable balloon located on the catheter for anchoring the catheter in a vessel in a body of a human or animal subject, and the device as claimed in claim 1 located adjacent the distal end of the catheter with at least a portion of the guide element of the device located within the balloon and a distal portion of the guide element extending from the balloon.

16. A balloon catheter as claimed in claim 15 in which an anchoring means for anchoring the guide element of the device comprises the balloon of the balloon catheter.

17. A balloon catheter as claimed in claim 15 in which the operating means for rotating the penetrating element in the guide element extends longitudinally through the main lumen extending through the catheter, and is of length to extend from the penetrating element through the main lumen of the catheter and outwardly of the catheter adjacent the proximal end thereof.

18. A device as claimed in claim 1 in which the distal cutting edge of the penetrating element extends around the first guide bore of the penetrating element.

19. A method for guiding one of a guide wire, a boring tool and an instrument into engagement with one of an occlusion in a vessel and a wall of the vessel in the body of a human or animal subject, the method comprising:
providing a penetrating element terminating in a distal cutting edge for cutting into and penetrating the one of the occlusion and the wall of the vessel,
providing a first guide bore extending through the penetrating element for accommodating and guiding the one of the guide wire, the boring tool and the instrument into engagement with the one of the occlusion and the wall of the vessel,
providing an external screw thread on the penetrating element,
locating the penetrating element in a second guide bore extending through a guide element and engaging the external screw thread of the penetrating element with internal screw thread in the second guide bore of the guide element,
anchoring the guide element in the vessel with a distal end of the second guide bore of the guide element adjacent the one of the occlusion and the wall of the vessel, and
rotating the penetrating element in the second guide bore of the guide element by an operating means engaged with the penetrating element adjacent the proximal end thereof, for urging the penetrating element into penetrating engagement with the one of the occlusion and the wall of the vessel, and guiding the one of the guide wire, the boring tool and the instrument through the first guide bore of the penetrating element into engagement with the one of the occlusion and the wall of the vessel.

20. A method as claimed in claim 19 in which the operating means is releasably engaged with the penetrating element.

21. A method as claimed in claim 19 in which an internal screw thread is provided in the first guide bore of the penetrating element for engaging and co-operating with a corresponding external screw thread on one of a boring tool, a guide wire and an instrument, and the one of the boring tool, the guide wire and the instrument is rotated in the first guide bore of the penetrating element with the external screw thread of the one of the boring tool, the guide wire and the instrument engaged with the internal screw thread in the first guide bore of the penetrating element for urging the one of the boring tool, the guide wire and the instrument through the first guide bore of the penetrating element.

\* \* \* \* \*